US007524495B2

United States Patent
Ullrich et al.

(10) Patent No.: US 7,524,495 B2
(45) Date of Patent: Apr. 28, 2009

(54) INHIBITION OF TACE OR AMPHIREGULIN FOR THE MODULATION OF EGF RECEPTOR SIGNAL TRANSACTIVATION

(75) Inventors: Axel Ullrich, Munich (DE); Andreas Gschwind, Munich (DE); Stefan Hart, Bruckberg (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 450 days.

(21) Appl. No.: 10/546,160

(22) PCT Filed: Feb. 20, 2004

(86) PCT No.: PCT/EP2004/001691

§ 371 (c)(1),
(2), (4) Date: Aug. 22, 2005

(87) PCT Pub. No.: WO2004/073734

PCT Pub. Date: Sep. 2, 2004

(65) Prior Publication Data

US 2006/0246448 A1    Nov. 2, 2006

(30) Foreign Application Priority Data

Feb. 21, 2003   (EP)   ................................ 03003935

(51) Int. Cl.
*A61K 39/395*   (2006.01)
*G01N 33/53*   (2006.01)
(52) U.S. Cl. ..................................... 424/130.1; 435/7.1
(58) Field of Classification Search ................. None
See application file for complete search history.

(56) References Cited

U.S. PATENT DOCUMENTS 5,830,995 A * 11/1998 Shoyab et al. ............... 530/322
6,180,403 B1   1/2001 Flournoy et al.

FOREIGN PATENT DOCUMENTS

EP   1 279 674 A   1/2003
WO   WO 92/02822 A   2/1992

OTHER PUBLICATIONS

Rudikoff et al (Proc Natl Acad Sci USA 1982; 79:1979).*
Ezzell (J. NIH Res, 1995, 7:46-49).*
http://children.webmd.com/tc/cystic-fibrosis-prevention.*
Spitler (Cancer Biotherapy, 1995, 10:1-3).*
Boon (Adv Can Res, 1992, 58:177-210).*
DeGruijl et al (Nature Medicine, 5410): 1124-1125, Oct. 1999).*
Gschwind et al., "Lysophaditidic Acid-Induced Squamous Cell Carcinoma Cell Proliferation . . . ", Cancer Research, American Association for Cancer Research, vol. 62, No. 21, Nov. 1, 2002, pp. 6329-6336.
Sunnarborg et al., "Tumor necrosis factor-alpha converting enzyme (TACE) . . . " The Journal of Biological Chemistry, vol. 277, No. 15, Apr. 12, 2002, pp. 12838-12845.
Gschwind et al., "TACE cleavage of proamphiregulin regulates GPCR-induced proliferation and motility of cancer cells", The EMBO Journal, vol. 22, No. 10, May 15, 2003, pp. 2411-2421.

* cited by examiner

*Primary Examiner*—Christopher H Yaen
(74) *Attorney, Agent, or Firm*—Rothwell, Figg, Ernst & Manbeck, P.C.

(57) ABSTRACT

The present invention relates to the modulation of transactivation of receptor tyrosine kinases by G protein or G protein-coupled receptor (GPCR) mediated signal transduction in a cell or an organism comprising inhibiting the activity of the metalloprotease TACE/ADAM17 and/or the activity of the receptor tyrosine kinase ligand amphiregulin.

7 Claims, 10 Drawing Sheets

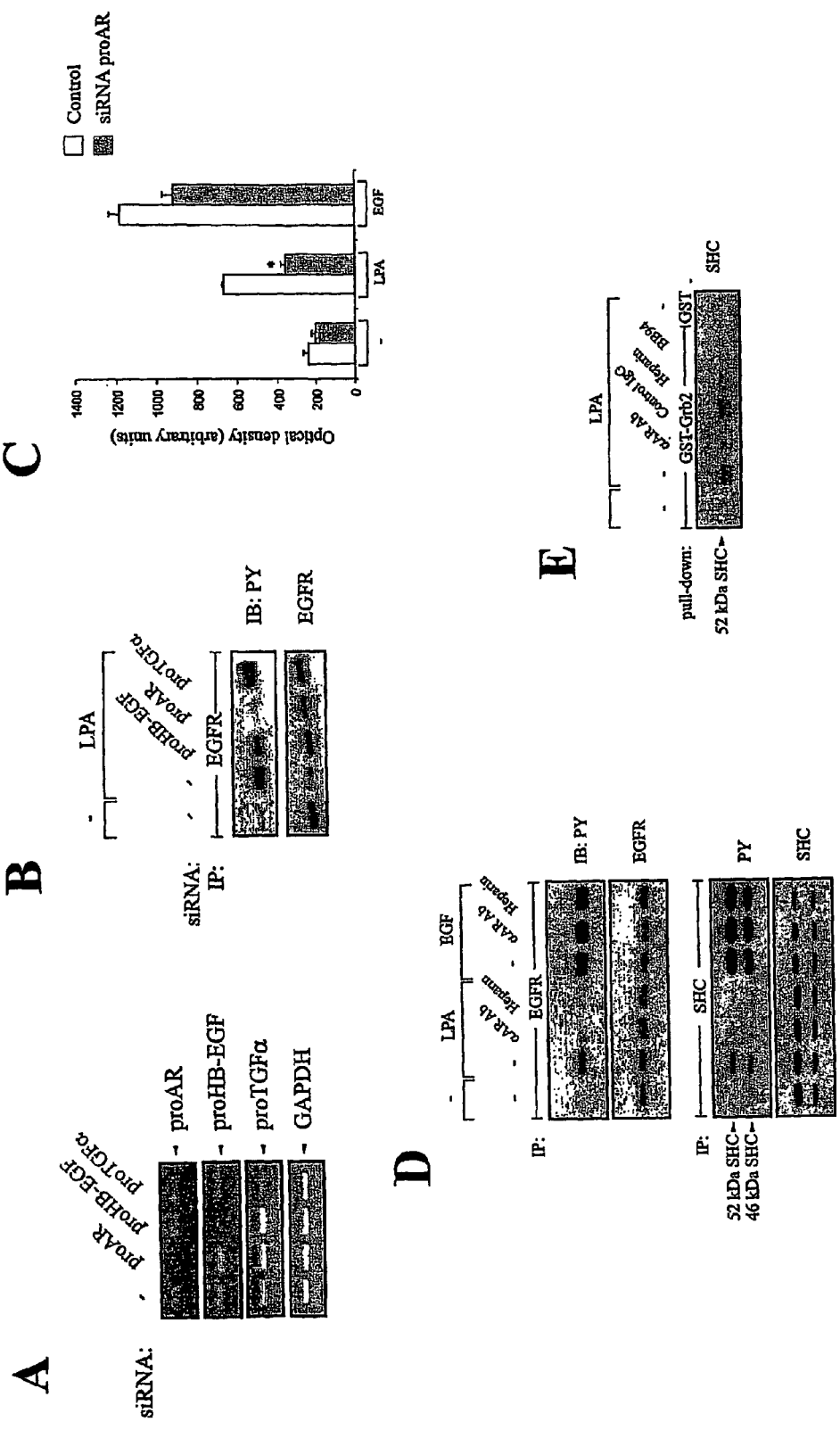

Figure 1:
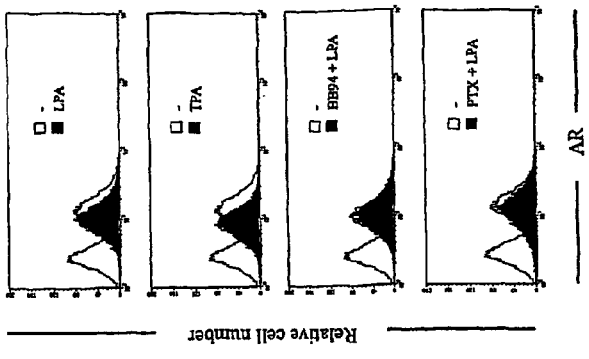
Figure 1:
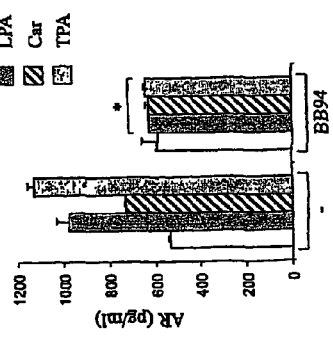
Figure 1:
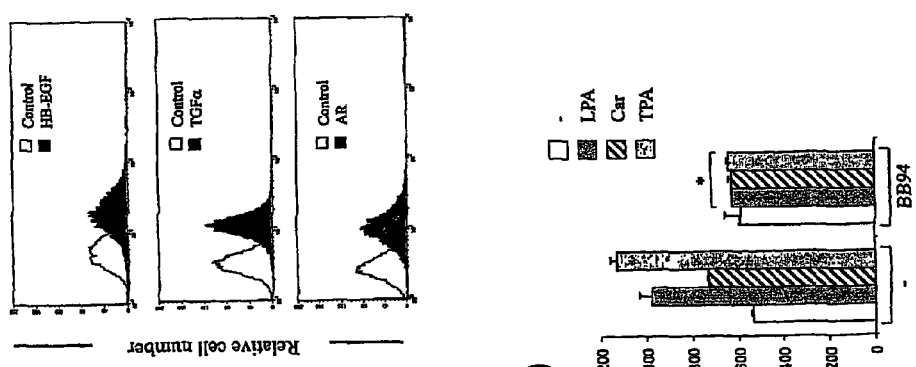
Figure 1:
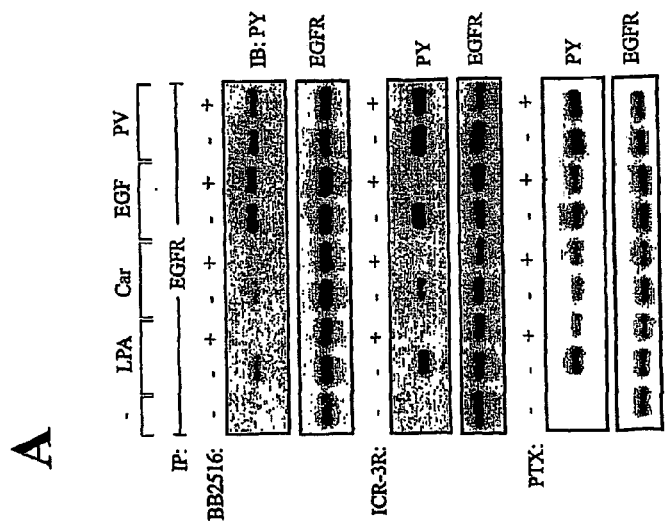

SEQUENCE LISTING

```
<160> NUMBER OF SEQ ID NOS: 22

<210> SEQ ID NO 1
<211> LENGTH: 21
<212> TYPE: DNA
<213> ORGANISM: Artificial
<220> FEATURE:
<223> OTHER INFORMATION: siRNA construct with homology to human sequence
<220> FEATURE:
<221> NAME/KEY: misc_feature
<222> LOCATION: (1)..(21)
<223> OTHER INFORMATION: RNA/DNA hybrid siRNA construct
<220> FEATURE:
<221> NAME/KEY: misc_feature
<222> LOCATION: (20)..(21)
<223> OTHER INFORMATION: dT

<400> SEQUENCE: 1
ccacaaauac cuggcuatat t                                              21

<210> SEQ ID NO 2
<211> LENGTH: 21
<212> TYPE: DNA
<213> ORGANISM: Artificial
<220> FEATURE:
```

<223> OTHER INFORMATION: siRNA construct with homology to human sequence
<220> FEATURE:
<221> NAME/KEY: misc_feature
<222> LOCATION: (1)..(21)
<223> OTHER INFORMATION: RNA/DNA hybrid siRNA construct
<220> FEATURE:
<221> NAME/KEY: misc_feature
<222> LOCATION: (20)..(21)
<223> OTHER INFORMATION: dT

<400> SEQUENCE: 2
aaauccaugu aaugcagaat t                                              21

<210> SEQ ID NO 3
<211> LENGTH: 21
<212> TYPE: DNA
<213> ORGANISM: Artificial
<220> FEATURE:
<223> OTHER INFORMATION: siRNA construct with homology to human sequence
<220> FEATURE:
<221> NAME/KEY: misc_feature
<222> LOCATION: (1)..(21)
<223> OTHER INFORMATION: RNA/DNA hybrid siRNA construct
<220> FEATURE:
<221> NAME/KEY: misc_feature
<222> LOCATION: (20)..(21)
<223> OTHER INFORMATION: dT

<400> SEQUENCE: 3
gugaaguugg gcaugacuat t                                              21

<210> SEQ ID NO 4
<211> LENGTH: 21
<212> TYPE: DNA
<213> ORGANISM: Artificial
<220> FEATURE:
<223> OTHER INFORMATION: siRNA construct with homology to human sequence
<220> FEATURE:
<221> NAME/KEY: misc_feature
<222> LOCATION: (1)..(21)
<223> OTHER INFORMATION: RNA/DNA hybrid siRNA construct
<220> FEATURE:
<221> NAME/KEY: misc_feature
<222> LOCATION: (20)..(21)
<223> OTHER INFORMATION: dT

<400> SEQUENCE: 4
uacaaggacu ucugcaucct t                                              21

<210> SEQ ID NO 5
<211> LENGTH: 21
<212> TYPE: DNA
<213> ORGANISM: Artificial
<220> FEATURE:
<223> OTHER INFORMATION: siRNA construct with homology to human sequence
<220> FEATURE:
<221> NAME/KEY: misc_feature
<222> LOCATION: (1)..(21)
<223> OTHER INFORMATION: RNA/DNA hybrid siRNA construct
<220> FEATURE:
<221> NAME/KEY: misc_feature
<222> LOCATION: (20)..(21)
<223> OTHER INFORMATION: dT

<400> SEQUENCE: 5
aacacuguga guggugccgt t                                              21

<210> SEQ ID NO 6
<211> LENGTH: 21
<212> TYPE: DNA
<213> ORGANISM: Artificial

```
<220> FEATURE:
<223> OTHER INFORMATION: siRNA construct with homology to human sequence
<220> FEATURE:
<221> NAME/KEY: misc_feature
<222> LOCATION: (1)..(21)
<223> OTHER INFORMATION: RNA/DNA hybrid siRNA construct
<220> FEATURE:
<221> NAME/KEY: misc_feature
<222> LOCATION: (20)..(21)
<223> OTHER INFORMATION: dT

<400> SEQUENCE: 6
gaagcaggcc aucaccgcct t                                             21

<210> SEQ ID NO 7
<211> LENGTH: 23
<212> TYPE: DNA
<213> ORGANISM: Artificial
<220> FEATURE:
<223> OTHER INFORMATION: siRNA construct with homology to human sequence
<220> FEATURE:
<221> NAME/KEY: misc_feature
<222> LOCATION: (1)..(23)
<223> OTHER INFORMATION: RNA/DNA hybrid siRNA construct
<220> FEATURE:
<221> NAME/KEY: misc_feature
<222> LOCATION: (22)..(23)
<223> OTHER INFORMATION: dT

<400> SEQUENCE: 7
aaaguuugcu uggcacaccu utt                                           23

<210> SEQ ID NO 8
<211> LENGTH: 23
<212> TYPE: DNA
<213> ORGANISM: Artificial
<220> FEATURE:
<223> OTHER INFORMATION: siRNA construct with homology to human sequence
<220> FEATURE:
<221> NAME/KEY: misc_feature
<222> LOCATION: (1)..(23)
<223> OTHER INFORMATION: RNA/DNA hybrid siRNA construct
<220> FEATURE:
<221> NAME/KEY: misc_feature
<222> LOCATION: (22)..(23)
<223> OTHER INFORMATION: dT

<400> SEQUENCE: 8
aaaguaaggc ccaggagugu utt                                           23

<210> SEQ ID NO 9
<211> LENGTH: 23
<212> TYPE: DNA
<213> ORGANISM: Artificial
<220> FEATURE:
<223> OTHER INFORMATION: siRNA construct with homology to human sequence
<220> FEATURE:
<221> NAME/KEY: misc_feature
<222> LOCATION: (1)..(23)
<223> OTHER INFORMATION: RNA/DNA hybrid siRNA construct
<220> FEATURE:
<221> NAME/KEY: misc_feature
<222> LOCATION: (22)..(23)
<223> OTHER INFORMATION: dT

<400> SEQUENCE: 9
aacauagagc cacuuuggag att                                           23

<210> SEQ ID NO 10
<211> LENGTH: 21
<212> TYPE: DNA
```

```
<213> ORGANISM: Artificial
<220> FEATURE:
<223> OTHER INFORMATION: siRNA construct with homology to human sequence
<220> FEATURE:
<221> NAME/KEY: misc_feature
<222> LOCATION: (1)..(21)
<223> OTHER INFORMATION: RNA/DNA hybrid siRNA construct
<220> FEATURE:
<221> NAME/KEY: misc_feature
<222> LOCATION: (20)..(21)
<223> OTHER INFORMATION: dT

<400> SEQUENCE: 10
ccucgcugca aagaaugugt t                                              21

<210> SEQ ID NO 11
<211> LENGTH: 21
<212> TYPE: DNA
<213> ORGANISM: Artificial
<220> FEATURE:
<223> OTHER INFORMATION: siRNA construct with homology to human sequence
<220> FEATURE:
<221> NAME/KEY: misc_feature
<222> LOCATION: (1)..(21)
<223> OTHER INFORMATION: RNA/DNA hybrid siRNA construct
<220> FEATURE:
<221> NAME/KEY: misc_feature
<222> LOCATION: (20)..(21)
<223> OTHER INFORMATION: dT

<400> SEQUENCE: 11
gaccuugata cgacugcugt t                                              21

<210> SEQ ID NO 12
<211> LENGTH: 21
<212> TYPE: DNA
<213> ORGANISM: Artificial
<220> FEATURE:
<223> OTHER INFORMATION: siRNA construct with homology to human sequence
<220> FEATURE:
<221> NAME/KEY: misc_feature
<222> LOCATION: (1)..(21)
<223> OTHER INFORMATION: RNA/DNA hybrid siRNA construct
<220> FEATURE:
<221> NAME/KEY: misc_feature
<222> LOCATION: (20)..(21)
<223> OTHER INFORMATION: dT

<400> SEQUENCE: 12
cguacgcgga auacuucgat t                                              21

<210> SEQ ID NO 13
<211> LENGTH: 20
<212> TYPE: DNA
<213> ORGANISM: Artificial
<220> FEATURE:
<223> OTHER INFORMATION: PCR Primer with homology to proAR

<400> SEQUENCE: 13
tggtgctgtc gctcttgata                                                20

<210> SEQ ID NO 14
<211> LENGTH: 20
<212> TYPE: DNA
<213> ORGANISM: Artificial
<220> FEATURE:
<223> OTHER INFORMATION: PCR primer with homology to proAR

<400> SEQUENCE: 14
gccaggtatt tgtggttcgt                                                20
```

<210> SEQ ID NO 15
<211> LENGTH: 20
<212> TYPE: DNA
<213> ORGANISM: Artificial
<220> FEATURE:
<223> OTHER INFORMATION: PCR primer with homology to pro HB-EGF

<400> SEQUENCE: 15
ttatcctcca agccacaagc                                          20

<210> SEQ ID NO 16
<211> LENGTH: 21
<212> TYPE: DNA
<213> ORGANISM: Artificial
<220> FEATURE:
<223> OTHER INFORMATION: PCR primer with homology to pro HB-EGF

<400> SEQUENCE: 16
tgaccagcag acagacagat g                                        21

<210> SEQ ID NO 17
<211> LENGTH: 20
<212> TYPE: DNA
<213> ORGANISM: Artificial
<220> FEATURE:
<223> OTHER INFORMATION: PCR primer with homology to pro TGFa

<400> SEQUENCE: 17
tgttcgctct gggtattgtg                                          20

<210> SEQ ID NO 18
<211> LENGTH: 20
<212> TYPE: DNA
<213> ORGANISM: Artificial
<220> FEATURE:
<223> OTHER INFORMATION: PCR primer with homology to pro TGFa

<400> SEQUENCE: 18
actgtttctg agtggcagca                                          20

<210> SEQ ID NO 19
<211> LENGTH: 20
<212> TYPE: DNA
<213> ORGANISM: Artificial
<220> FEATURE:
<223> OTHER INFORMATION: PCR primer with homology to TACE

<400> SEQUENCE: 19
cgcattctca agtctccaca                                          20

<210> SEQ ID NO 20
<211> LENGTH: 20
<212> TYPE: DNA
<213> ORGANISM: Artificial
<220> FEATURE:
<223> OTHER INFORMATION: PCR primer with homology to TACE

<400> SEQUENCE: 20
tatttccctc cctggtcctc                                          20

<210> SEQ ID NO 21
<211> LENGTH: 20
<212> TYPE: DNA
<213> ORGANISM: Artificial
<220> FEATURE:

```
<223> OTHER INFORMATION: PCR primer with homology to ADAM12

<400> SEQUENCE: 21
cagtttcacg gaaacccact                                              20

<210> SEQ ID NO 22
<211> LENGTH: 20
<212> TYPE: DNA
<213> ORGANISM: Artificial
<220> FEATURE:
<223> OTHER INFORMATION: PCR primer with homology to ADAM12

<400> SEQUENCE: 22
gaccagaaca cgtgctgaga                                              20
```

INHIBITION OF TACE OR AMPHIREGULIN FOR THE MODULATION OF EGF RECEPTOR SIGNAL TRANSACTIVATION

CROSS REFERENCE TO RELATED APPLICATION

This application is a 35 USC § 371 National Phase Entry Application from PCT/EP2004/001691, filed Feb. 20, 2004, and designating the United States.

The present invention relates to the modulation of transactivation of receptor tyrosine kinases by G protein or G protein-coupled receptor (GPCR) mediated signal transduction in a cell or an organism comprising inhibiting the activity of the metalloprotease TACE/ADAM17 and/or the activity of the receptor tyrosine kinase ligand amphiregulin.

Communication between G protein-coupled receptor (GPCR) and EGFR signalling systems involves cell surface proteolysis of the growth factor precursor proHB-EGF (1-3). The molecular mechanism of EGFR signal transactivation in human cancer cells, however, is largely unknown.

Interreceptor communication between G protein-coupled receptors (GPCRs) and the EGFR occurs in diverse cell types including fibroblasts, keratinocytes and smooth muscle cells (4). Treatment of cells with GPCR agonists results in activation and tyrosine phosphorylation of the EGFR and subsequently leads to the generation of an EGFR-characteristic, intracellular signal (5). Due to the rapid kinetics of the EGFR transactivation signal and the fact that release of EGFR ligands was not detectable after GPCR stimulation, the mechanism of EGFR transactivation was proposed to exclusively rely on intracellular elements (5, 6). In contrast, a novel mechanistic concept of EGFR transactivation involves the proteolytic release of heparin-binding EGF-like growth factor (HB-EGF) at the cell surface of GPCR stimulated cells (1). HB-EGF, as well as transforming growth factor alpha (TGFa) and amphiregulin (AR) belong to a family of EGF-like ligands that directly activate the EGFR. These molecules are synthesized as transmembrane precursors and are subject to proteolytic cleavage to produce the soluble and diffusible growth factors (7). The HB-EGF-dependent mechanism of EGFR signal transactivation has gained further experimental support by studies on GPCR mitogenic signalling in vascular smooth muscle cells (8), cardiac endothelial cells (9) and cardiomyocytes (10). Importantly, recent data have implicated EGFR signal transactivation pathways in the etiology of pathobiological processes such as cystic fibrosis (3), cardiac (2) and gastrointestinal hypertrophy (11). Furthermore, increasing evidence argues for a direct correlation between aberrant GPCR signalling and the development and progression of human cancers (12). We have recently demonstrated that GPCR-EGFR cross-talk pathways are widely established in head and neck squamous cell carcinoma (HNSCC) cells and that GPCR agonists such as LPA and carbachol regulate the proliferative and migratory behavior of HNSCC cells via transactivation of the EGFR (13). Elucidation of the molecular mechanisms underlying EGFR signal transactivation may thus lead to new strategies for the prevention and treatment of carcinomas, e.g. squamous cell carcinomas.

Here, we demonstrate that in squamous cell carcinoma cells stimulation with the GPCR agonists lysophosphatidic acid (LPA) or carbachol specifically results in metalloprotease-dependent cleavage and release of the EGFR ligand amphiregulin (AR). Moreover, AR gene silencing by small interfering RNA (siRNA) or inhibition of AR biological activity by neutralizing antibodies prevents GPCR-induced EGFR tyrosine phosphorylation, downstream mitogenic signalling events, activation of Akt/PKB, cell proliferation and migration. Furthermore, we present evidence that in squamous cell carcinoma cells blockade of the metalloprotease-disintegrin TACE/ADAM17 by expression of a dominant negative mutant or by RNA interference suppresses GPCR stimulated AR release and EGFR-dependent cellular responses. Thus, TACE and/or AR can function as an effector of GPCR-mediated signalling and therefore represents a key element of the cellular receptor cross-talk network.

In a first aspect, the invention relates to a method for modulating transactivation of receptor tyrosine kinases by G protein or G protein-coupled receptor mediated signal transduction in a cell comprising inhibiting the activity of the metalloprotease TACE/ADAM17 and/or the activity of the receptor tyrosine kinase ligand amphiregulin.

The term "inhibition" according to the present invention preferably relates to a "specific" inhibition, wherein the activity of TACE/ADAM17 and/or amphiregulin is selectively inhibited, i.e. the activity of other metalloproteases such as ADAM12 or other receptor tyrosine kinase ligands such as HB-EGF is not significantly inhibited. By means of selective inhibition of TACE/ADAM17 and/or amphiregulin a highly specific disruption of receptor tyrosine kinase transactivation may be achieved which is important for pharmaceutical applications in that the occurance of undesired side effects may be reduced.

Further, the term "inhibition" preferably relates to a "direct" inhibition, wherein the inhibitor directly binds to TACE/ADAM17 and/or amphiregulin or a nucleic acid molecule coding therefor. The invention, however, also encompasses an "indirect" inhibtion wherein the inhibitor does not directly bind to TACE/ADAM17 and/or amphiregulin but to a precursor or metabolite thereof, particularly the amphiregulin precursor proamphiregulin.

The term "activity" preferably relates to the cleavage of proamphiregulin by TACE/ADAM17 and/or the activation of a receptor tyrosine kinase, e.g. EGFR by amphiregulin. A TACE/ADAM17 inhibitor of the present invention is preferably capable of inhibiting the cleavage and release of the receptor tyrosine kinase ligand amphiregulin. An amphiregulin inhibitor of the present invention is preferably capable of inhibiting biological activity of amphiregulin, particularly EGFR tyrosine phosphorylation, downstream mitogenic signaling events, activation of Akt/PKB, cell proliferation and/or migration.

A further aspect of the present invention is the use of an inhibitor of the metalloprotease TACE/ADAM17 and/or an inhibitor of the receptor tyrosine kinase ligand amphiregulin for the prevention and/or treatment of a disorder which is caused by or associated with a transactivation of receptor tyrosine kinases by G protein oder G protein-coupled receptor mediated signal transduction. The presence of such a type of disorder may be determined by measuring G protein and/or GPCR expression, e.g. on the mRNA level (cDNA array analysis, SAGE, Northern blot, etc.) and/or on the protein level (Western blot analysis, Immunofluorescence Microscopy, in situ hybridisation techniques, etc.). The presence of such a type of disorder may also be determined by examining the occurrence of activating mutations in genomic and/or mRNA molecules encoding G proteins or GPCRs and/or the presence of virally encoded GPCRs. Further, elevated levels of GPCR agonists such as LPA and/or amphiregulin in serum and/or disease-affected tissues may be determined. It should be pointed out that this type of disorder need not be associated with enhanced receptor tyrosine kinase expression.

For example, the disorder may be a hyperproliferative disorder such as cancer, e.g. squamous cell carcinoma or another disorder such as a hyperproliferative skin disease, e.g. psoriasis.

The activity of TACE/ADAM17 and/or amphiregulin may be inhibited on the nucleic acid level, e.g. on the gene level or on the transcription level. Inhibition on the gene level may comprise a partial or complete gene inactivation, i.e. by gene disruption. On the other hand, inhibition may occur on the transcript level, e.g. by application of antisense molecules, e.g. DNA molecules, RNA molecules or nucleic acid analogues, ribozymes, e.g. RNA molecules or nucleic acid analogues or small RNA molecules capable of RNA interference (RNAi), e.g. RNA molecules or nucleic acid analogues, directed against TACE/ADAM17 and/or amphiregulin mRNA. Antisense molecules inhibiting the expression of TACE/ADAM17 are for example described in U.S. Pat. No. 6,180,403, which is herein incorporated by reference.

Further, the activity of TACE/ADAM17 and/or amphiregulin may be inhibited on the protein level, e.g. by application of compounds which result in a specific inhibition of TACE/ADAM17 and/or amphiregulin acitivity. The inhbition on the protein level may comprise for example the application of antibodies or antibody fragments directed against TACE/ADAM17 and/or amphiregulin. The antibodies may be polyclonal antibodies or monoclonal antibodies, recombinant antibodies, e.g. single chain antibodies or fragments of such antibodies which contain at least one antigen-binding site, e.g. proteolytic antibody fragments such as Fab, Fab' or F(ab')2 fragments or recombinant antibody fragments such as scFv fragments. For therapeutic purposes, particularly for the treatment of humans, the application of chimeric antibodies, humanized antibodies or human antibodies is especially preferred.

The antibodies or antibody fragments may be directed against the metalloprotease-domain of TACE/ADAM17, or against other parts of the molecule. The antibodies or antibody fragments may selectively recognize the mature form of TACE/ADAM17, or the pro-form of TACE/ADAM17 as shown by immunoprecipitation. Alternatively, the antibodies or antibody fragments may recognize both the mature form and the pro-form of TACE/ADAM17.

Monoclonal antibodies may be generated by known techniques, e.g. hybridoma techniques as described by Köhler et al. (Nature 256 (1975), 495-497), Cole et al. (Mol. Cell. Biol. 62 (1984), 109-120) or Kozbor et al. (J. Immunol. Meth. 81 (1985), 31-42) which are herein incorporated by reference. Chimeric or humanized antibodies may be generated by techniques described by Morrison et al. (Proc. Natl. Acad. Sci. USA 81 (1984), 6851-6855), Neuberger et al. (Nature 312 (1984), 604-608), Takeda et al. (Nature 314 (1985), 452-454), Jones et al. (Nature 321 (1986), 522-525), Riechmann et al. (Nature 322 (1988), 323-327), Verhoeyen et al. (Science 239 (1988), 1534-1536) or Queen et al. (Proc. Natl. Acad. Sci. USA 86 (1989), 10029-10033), which are herein incorporated by reference. Further methods for generating antibodies or antibody fragments are described by Burton (Proc. Natl. Acad. Sci. USA 88 (1991), 11120-11123), Orlandi et al., (Proc. Natl. Acad. Sci. USA 86 (1989), 3833-3837), Winter et al. (Nature 349 (1991), 293-299) or Huse et al. (Science 254 (1989), 1275-1281), which are herein incorporated by reference.

Furthermore, low-molecular weight inhibitors of TACE/ADAM17 and/or amphiregulin may be used. Examples of TACE/ADAM17 inhibitors are sulfonic acid or phosphinic acid derivatives, e.g. sulfonamides, sulfonamide hydroxamic acids, phosphinic acid amide hydroxamic acids, e.g. as described in WO 98/16503, WO 98/16506, WO 98/16514, WO 98/16520, Mac Pherson et al. (J. Med. Chem. 40, (1997), 2525), Tamura et al. (J. Med. Chem. 41 (1998), 690), Levin et al. (Bioorg. & Med. Chem. Lett. 8 (1998), 2657), Pikul et al. (J. Med. Chem. 41 (1998), 3568), WO 97/18194, EP-A-0803505, WO 98/08853, WO 98/03166 and EP-A-1279674, which are herein incorporated by reference. Further inhibitors may be identified by screening procedures as outlined in detail below.

For therapeutic purposes, the medicament is administered in the form of a pharmaceutical composition which additionally comprises pharmaceutically acceptable carriers, diluents and/or adjuvants.

Pharmaceutical compositions suitable for use in the present invention include compositions wherein the active ingredients are contained in an effective amount to achieve its intended purpose. A therapeutically effective dose refers to that amount of the compound that results in amelioration of symptoms or a prolongation of survival in a patient. Toxicity and therapeutic efficacy of such compounds can be determined by standard pharmaceutical procedures In cell cultures or experimental animals, e.g. for determining the LD50 (the dose lethal to 50% of the population) and the ED50 (the dose therapeutically effective in 50% of the population). For any compound used in the method of the invention, the therapeutically effective dose can be estimated initially from cell culture assays. For example, a dose can be formulated in animal models to achieve a circulating concentration range that includes the IC50 as determined in cell culture (i.e. the concentration of the test compound which achieves a half-maximal inhibition of the growth-factor receptor activity). Such information can be used to more accurately determine useful doses in humans. The dose ratio between toxic and therapeutic effects is the therapeutic index and it can be expressed as the ratio between LD50 and ED50. Compounds which exhibit high therapeutic indices are preferred. The exact formulation, route of administration and dosage can be chosen by the individual physician in view of the patient's condition (see e.g. Fingl et al., 1975, in "The Pharmacological Basis of Therapeutics", Ch. 1, p. 1).

Dosage amount and interval may be adjusted individually to provide plasma levels of the active moiety which are sufficient to maintain the receptor modulating effects, or minimal effective concentration (MEC). The MEC will vary for each compound but can be estimated from in vitro data, e.g. the concentration necessary to achieve a 50-90% inhibition of the receptor using the assays described herein. Compounds should be administered using a regimen which maintains plasma levels above the MEC for 10-90% of the time, preferably between 30-90% and most preferably between 50-90%. Dosages necessary to achieve the MEC will depend on individual characteristics and route of administration. In cases of local administration or selective uptake, the effective local concentration of the drug may not be related to plasma concentration.

The actual amount of composition administered will, of course, be dependent on the subject being treated, on the subject's weight, the severity of the affliction, the manner of administration and the judgement of the prescribing physician. For antibodies or therapeutically active nucleic acid molecules, and other compounds e.g. a daily dosage of 0.001 to 100 mg/kg, particularly 0.01 to 10 mg/kg per day is suitable.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systematic manner, for example, via injection of the compound directly into a solid tumor, often in a depot or sustained release formulation.

Furthermore, one may administer the drug in a targeted drug delivery system, for example in a liposome coated with a tumor-specific antibody. The liposomes will be targeted to and taken up selectively by the tumor.

Still a further aspect of the present invention is a method for identifying modulators of receptor tyrosine kinase transactivation by G protein or G protein-coupled receptor mediated signal transduction, comprising determining, if a test compound is capable of inhibiting the activity of TACE/ADAM17 and/or the activity of amphiregulin. This method is suitable as a screening procedure, e.g. a high-throughput screening procedure for identifying novel compounds or classes of compounds which are capable of modulating G protein signal transduction. Further, the method is suitable as a validation procedure for characterizing the pharmaceutical efficacy and/or the side effects of compounds. The method may comprise the use of isolated proteins, cell extracts, recombinant cells or transgenic non-human animals. The recombinant cells or transgenic non-human animals preferably exhibit an altered TACE/ADAM17 and/or amphiregulin expression compared to a corresponding wild-type cell or animal.

Examples of suitable receptor tyrosine kinases are EGFR and other members of the EGFR family such as HER2, HER3 or HER4, PDGFR, the vascular endothelial growth factor receptor KDR/Flk-1, the Trk receptor, FGFR-1 or IGF-1 receptor but also other types of growth-factor receptors such as TNF receptor 1, TNF receptor 2, CD30 and IL-6 receptor are targets for the G protein/GPCR mediated signal transduction.

Furthermore, the invention should be explained by the following Figures and Examples.

FIG. 1 GPCR stimulation of the EGFR Involves a ligand-dependent mechanism and is accompanied by AR release from the cell surface. a, EGFR signal transactivation requires metalloprotease activity and the EGFR extracellular domain. SCC-9 cells were pre-incubated with marimastat (BB2516, 10 µM; 20 min), anti-EGFR antibody ICR-3R (20 µg/mL; 60 min) or PTX (100 ng/mL; 18 h) and treated with LPA (10 µM), carbachol (Car, 1 mM), EGF (7.5 ng/mL) or pervanadate (PV, 1 mM) for 3 min. Following immunoprecipitation (IP) of cell extracts with anti-EGFR antibody proteins were immunoblotted (IB) with anti-phosphotyrosine antibody and re-probed with anti-EGFR antibody. b, Flow cytometric analysis of EGF-like precursor expression. SCC-9 cells were collected and stained for surface HB-EGF, TGFa or AR and analyzed by flow cytometry. Control cells were labelled with FITC-conjugated secondary antibody alone. c, LPA-induced proteolytic processing of proAR. SCC-9 cells were pre-incubated with batimastat (BB94, 10 µM) or PTX and stimulated with LPA or TPA (1 µM) for 5 min. Cells were collected and analyzed for cell surface AR density by flow cytometry. d, GPCR-induced proteolytic release of AR. SCC-9 cells were pre-incubated with batimastat or vehicle followed by stimulation with agonists as indicated for 120 min. Conditioned medium was collected and analyzed for total AR amount by ELISA. Each bar is the average of triplicate values (mean±s.d.). *, P<0.03 for the difference between agonists vs. BB94+agonists.

Figure 2:
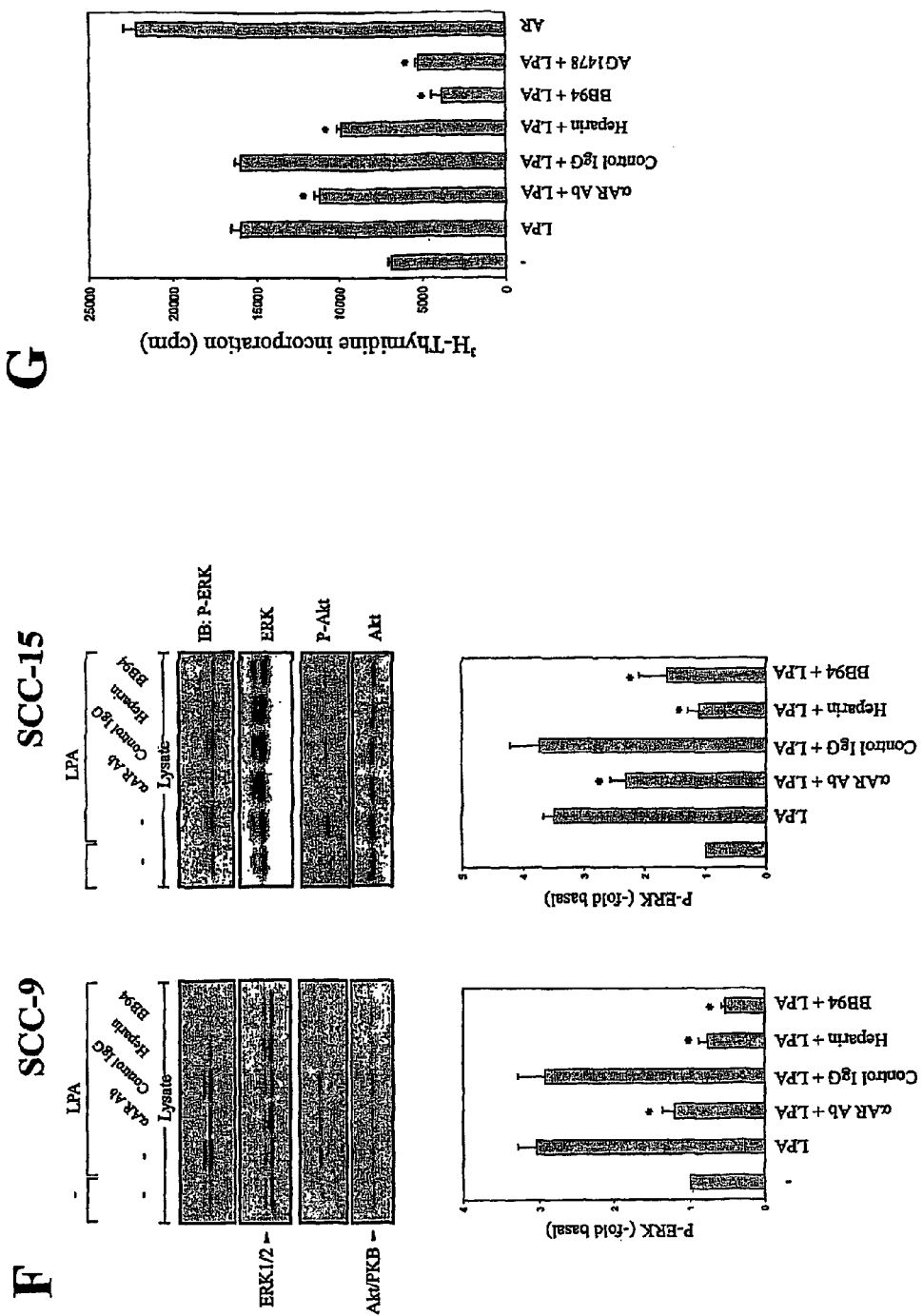

FIG. 2 GPCR stimulation requires AR to trigger EGFR-dependent signals and biological responses. a, Blockade of EGF-like growth factor precursor expression by RNA interference (RNAi). SCC-9 cells were transfected with siRNA for proAR, proHB-EGF or proTGFα cultured for 2 days and analyzed for gene expression by RT-PCR as indicated or b, stimulated with LPA or carbachol and assayed for EGFR tyrosine phosphorylation content. c, Requirement of AR for LPA-induced cell migration. SIRNA-transfected SCC-9 cells were analyzed for transwell migration toward fibronectin as chemoattractant. Each bar is the average of quadruplicate values (mean±s.d.). *, P<0.001 for control siRNA+LPA vs. proAR siRNA+LPA. d, Effect of anti-AR neutralizing antibody and heparin on GPCR-induced EGFR and SHC tyrosine phosphorylation. SCC-9 cells were pre-treated with anti-AR antibody (aARAb, 50 µg/mL, 60 min) or heparin (100 ng/mL, 15 min), and stimulated for 3' min (EGFR) or 5 min (SHC) as indicated. Precipitated EGFR and SHC were immunoblotted with anti-phosphotyrosine antibody followed by reprobing of the same filters with anti-EGFR and anti-SHC antibody, respectively. e, Association of Grb2 with SHC in vitro. SCC-9 cells were pre-incubated with inhibitors and stimulated for 5 min as indicated. Lysates were incubated with GST-Grb-2 fusion protein or GST alone. Proteins were immunoblotted with monoclonal anti-SHC antibody. f, AR is required for GPCR-induced ERK/MAPK activation and Akt/PKB phosphorylation. SCC-9 or SCC-15 cells were pre-incubated with inhibitors and stimulated for 7' min. Phosphorylated ERK1/2 was detected by immunoblotting total lysates with anti-phospho-ERK antibody. The same filters were re-probed with anti-ERK antibody. Quantitative analysis of ERK phosphorylation from three independent experiments (mean±s.d.). *, P<0.05 for the difference between LPA vs. inhibitors+LPA. Stimulation of Akt/PKB. Cell lysates were immunoblotted with anti-phospho-Akt/PKB antibody followed by reprobing of the same filters with anti-Akt/PKB antibody. g, Effect of AR inhibition on LPA-induced DNA synthesis. SCC-15 cells were treated with inhibitors as indicated and incubated in the presence or absence of ligands (LPA; AR, 10 ng/ml) for 18 h. Cells were then pulse-labelled with $^3$H-thymidine and thymidine incorporation was measured by liquid-scintillation counting. Quantitative analysis from three independent experiments (mean±s.d.). *, P<0.001 for LPA vs. inhibitors+LPA.

Figure 3:
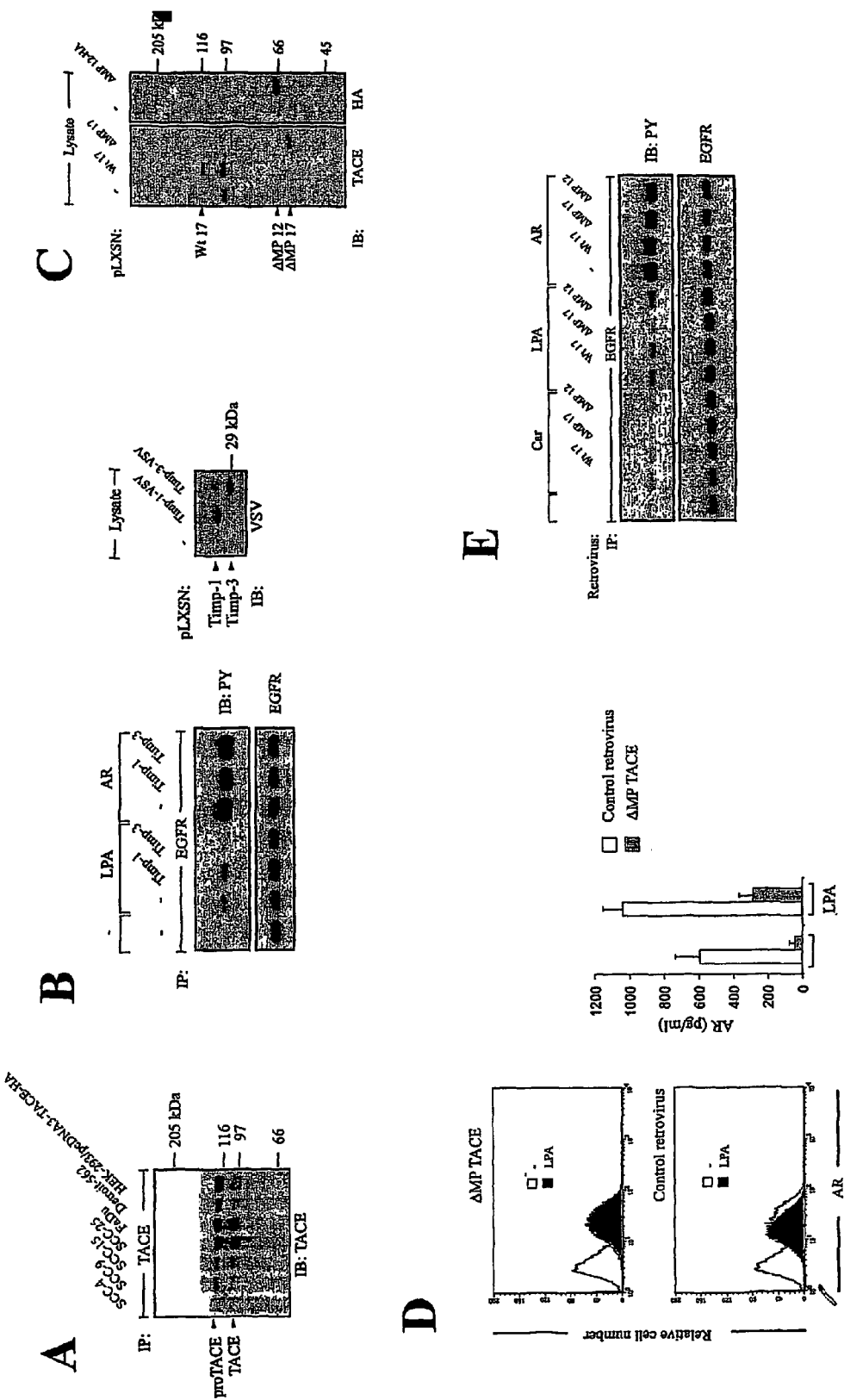

FIG. 3 Dominant negative TACE suppresses GPCR-induced AR release and EGFR signal transactivation. a, TACE is expressed in HNSCC cell lines. TACE was immunoprecipitated from lysates with monoclonal TACE/ADAM17 antibody. HEK-293 cells transfected with human TACE cDNA served as a positive control. b, Timp-3 but not Timp-1 inhibits EGFR signal transactivation. SCC-9 cells were infected with retrovirus encoding human Timp-1 or Timp-3. EGFR activation was determined by immunoblot after stimulation with agonists as indicated (left panel). Expression of Timp-1/3 carrying C-terminal VSV-tag was confirmed by immunoblotting total cell lysates with anti-VSV antibody (right panel). c, Expression of wild type and dominant negative TACE or HA-tagged ADAM12 in SCC-9 cells after retroviral gene transfer. Total lysates were immunoblotted as indicated. d, Dominant negative TACE abrogates LPA-induced proAR cleavage (left panel) and AR release into cell culture medium (right panel) as determined by flow cytometric analysis and AR ELISA, respectively. e, Effect of dominant negative TACE on GPCR stimulated EGFR signal transactivation.

Figure 4:
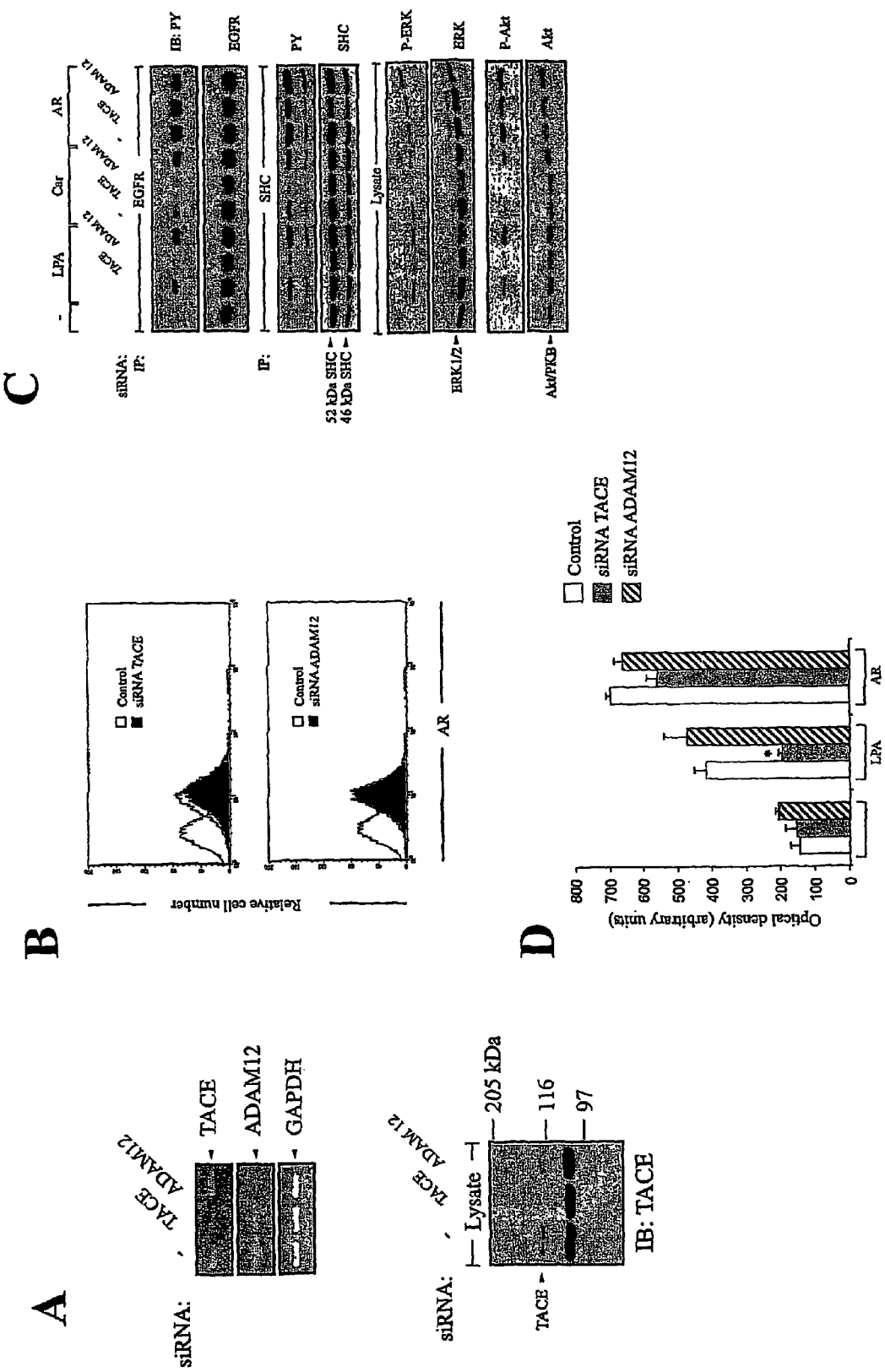

FIG. 4 TACE siRNA inhibits EGFR signal transmission and cell migration by GPCR agonists. a, TACE siRNA blocks endogenous TACE expression. SCC-9 cells were transfected with TACE or ADAM12 siRNA. Gene expression was analyzed by RT-PCR (left panel) or immunoblot (right panel) with polyconal anti-TACE antibody. b, Knockdown of TACE results in accumulation of proAR at the cell surface. siRNA-transfected SCC-9 cells were analyzed for AR cell surface content by FACS. c, EGFR signal transmission upon GPCR activation requires TACE. SCC-9 cells were transfected with siRNA and stimulated with agonists as indicated. Activation of EGFR, SHC, ERK and Akt was determined as described above. d, Squamous cancer cell motility in response to LPA depends on TACE. siRNA-transfected SCC-9 cells were treated with LPA or AR and analyzed in transwell migration assay.

Figure 5:
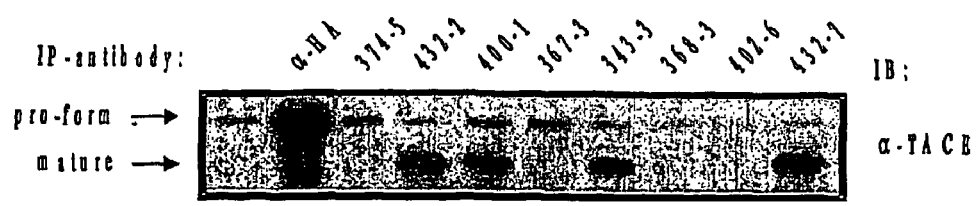

FIG. 5 Immunoprecipitation of mature TACE protein by monoclonal antibodies raised against the metalloprotease-domain. HEK-293 cells transiently expressing TACE-Hemagglutinin (HA) were serum-starved for 24 h and lysed with TritonX-100 lysis buffer containing 5 µM BB94 as metalloprotease inhibitor. 200 µg of crude lysate was used for immunoprecipitation with 5 µg contol IgG (monoclonal anti-HA antibody) or 5 µg monoclonal anti-TACE antibody. Following SDS-polyacrylamide gel electrophoresis, proteins were transferred to nitrocellulose membrane. Immunoprecipitated TACE protein was analysed by immunoblotting with polyclonal TACE antibody (CHEMICON #19027).

Figure 6:
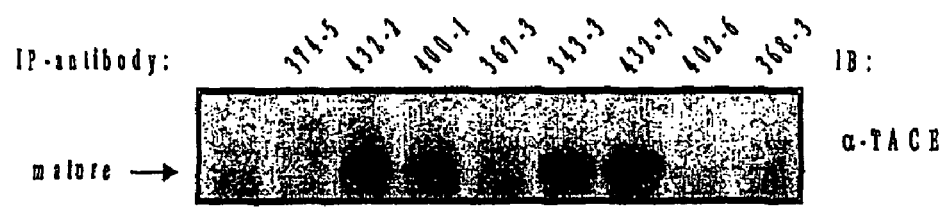

FIG. 6 immunoprecipitation of endogenous TACE protein. SCC-9 cells were serum-starved for 24 h and lysed with TritonX-100 lysis buffer containing 5 µM BB94 as metalloprotease inhibitor. 200 µg of crude lysate was used for immunoprecipitation with 5 µg contol IgG (monoclonal anti-HA antibody) or 5 µg monoclonal anti-TACE antibody. Following SDS-polyacrylamide gel electrophoresis, proteins were transferred to nitrocellulose membrane. Immunoprecipitated TACE protein was analysed by immunoblotting with TACE antibody (polyclonal antibody CHEMICON 19027).

Figure 7:
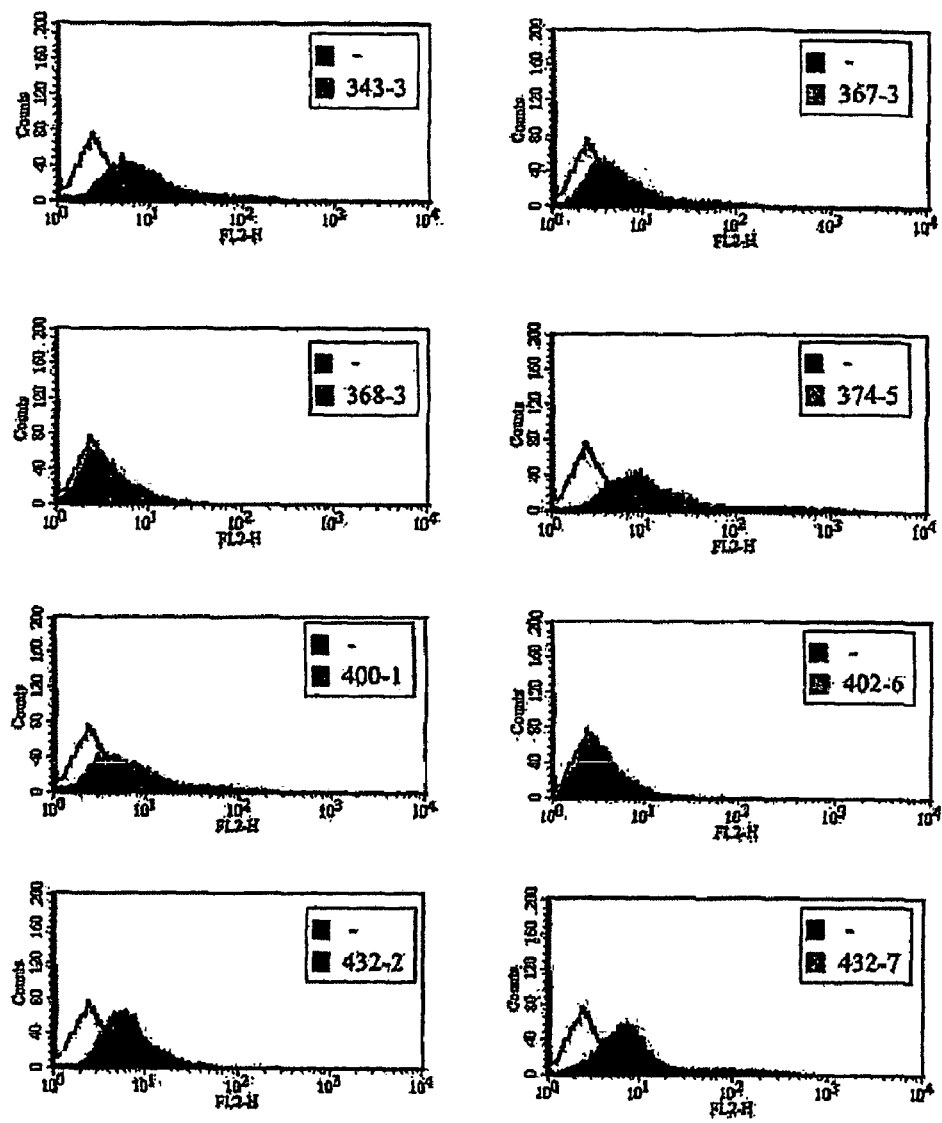

FIG. 7 Flow cytometric analysis of TACE-binding of monoclonal antibodies. SCC9-cells were seeded, grown for 24 h. After collection, cells were stained with monoclonal TACE antibodies raised against the metalloprotease domain of TACE for 45 min. After washing with phosphate-buffered saline (PBS), cells were incubated with phycoerythrin (PE)-conjugated secondary antibodies for 45 min and washed again with PBS. Cells were analysed on a Becton Dickinson FACScalibur Fow cytometer.

Figure 8:
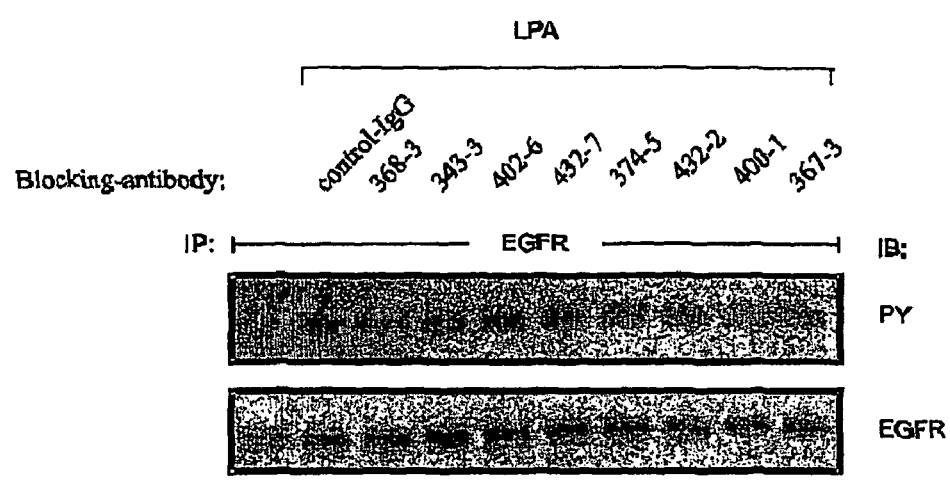

FIG. 8 EGFR signal transactivation requires TACE activity. Serum-starved SCC9 cells were preincubated for 30 minutes with 5 µg control IgG (monoclonal anti-HA antibody) or 5 µg monoclonal TACE antibody as indicated and treated with LPA (10 µM) for 3 min. After lysis, EGFR was immunoprecipitated (IP) using anti-EGFR antibody. Tyrosine-phosphorylated EGFR was detected by immunoblotting (IB) with anti-phosphotyrosine (αPY) antibody, followed by reprobing of the same filter with anti-EGFR antibody.

Figure 9:
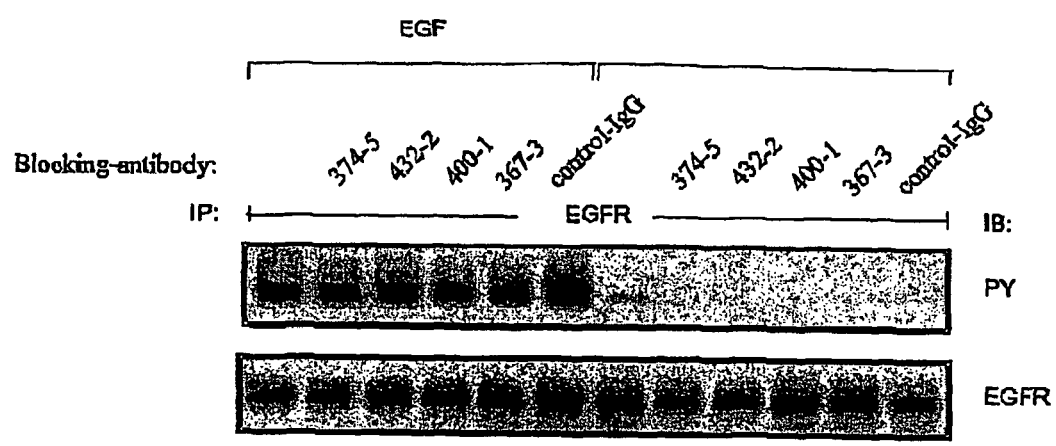

FIG. 9 EGFR signal transactivation requires TACE activity. Serum-starved SCC9 cells were preincubated for 30 minutes with 5 µg control IgG (monoclonal anti-HA antibody) or 5 µg monoclonal TACE antibody as indicated and treated with LPA (10 µM) for 3 min. After lysis, EGFR was immunoprecipitated (IP) using anti-EGFR antibody. Tyrosine-phosphorylated EGFR was detected by immunoblotting (IB) with anti-phosphotyrosine (αPY) antibody, followed by reprobing of the same filter with anti-EGFR antibody.

EXAMPLE 1

EGFR Signal Transactivation in Squamous Cell Carcinoma Requires Proamphiregulin Cleavage by TACE 1. Methods 1.1 Cell Culture, Plasmids and Retroviral Infections All cell lines (American Type Culture Collection, Manassas, Va.) were routinely grown according to the supplier's instructions. Transfections of HEK-293 cells were carried out by calcium phosphate coprecipitation as previously described (1). Anti-amphiregulin (AR), anti-HB-EGF neutralizing antibodies (R&D Systems, Minneapolis, Minn.), PTX, heparin (Sigma, St. Louis, Mo.), marimastat (BB2516, Sugen Inc., South San Francisco, Calif.), batimastat (BB94, British Biotech, Oxford, UK) were added to serum-starved cells before the respective growth factor.

Full-length cDNAs encoding ADAM10, 12, 15 and 17 were amplified by PCR from a human placenta cDNA library and subcloned into pcDNA3 (Invitrogen, Carlsbad, Calif.) and pLXSN vectors (Clontech, Palo Alto, Calif.). For virus production dominant negative protease constructs lacking the pro- and metalloprotease domains were generated as described before (2,26). All protease constructs included a C-terminal hemagglutinin (HA) tag, detectable with an anti-HA monoclonal antibody (Babco, Richmond, Calif.). The amphotropic packaging cell line Phoenix was transfected with pLXSN retroviral expression plasmids by the calcium phosphate/chloroquine method as described previously (29). At 24 h after transfection, the viral supernatant was collected and used to infect subconfluent SCC-9 cells (5×104 cells/6-Well plate).

1.2 Protein Analysis

Cells were lysed and proteins immunoprecipitated as described (13). Western blots were performed according to standard methods. The antibodies against human EGFR (108.1) and SHC (1), as well as a GST-Grb2 fusion protein (5), have been characterized before. Phosphotyrosine was detected with the 4G10 monoclonal antibody (UBI, Lake Placid, N.Y.). Polyclonal anti-phospho-p44/p42 (Thr202/Tyr204) MAPK antibody and anti-phospho-Akt (Ser473) antibody were purchased from New England Biolabs (Beverly, Mass.). Polyclonal anti-Akt1/2 and anti-ERK2 antibody was from Santa Cruz Biotechnology (Santa Cruz, Calif.), anti-TACE antibodies from Chemicon (Harrow, UK).

1.3 Flow Cytometric Analysis and ELISA

ACS analysis was performed as described before (1). Cells were stained with ectodomain-specific antibodies against HB-EGF, AR (R&D Systems) or TGFa (Oncogene, Boston; Mass.). After washing with PBS, cells were incubated with FITC-conjugated secondary antibody and analyzed on a Becton Dickinson FACScalibur flow cytometer.

Concentrations of free AR were determined by sandwich ELISA (R&D Systems) using monoclonal anti-AR capture antibody and biotinylated polyclonal detection antibody. Standards were recombinant human AR diluted in culture medium. For statistical analysis Student's t-test was used to compare data between two groups. Values are expressed as mean±s.d. of at least triplicate samples. $P<0.05$ was considered statistically significant.

1.4 RNA Interference and RT-PCR Analysis

Transfection of 21-nucleotide siRNA duplexes (Dharmacon Research, Lafayette, Colo., USA) for targeting endogenous genes was carried out using Oligofectamine (Invitrogen) and 4.2 µg siRNA duplex per 6-well plate as previously described (30). Transfected SCC-9 cells were serum-starved and assayed 4 d after transfection. Highest efficiencies in silencing target genes were obtained by using mixtures of siRNA duplexes targeting different regions of the gene of interest. Sequences of siRNA used were CCACAAAUACCUGGCUAUAdTdT, (SEQ ID NO:1)

AAAUCCAUGUAAUGCAGAAdTdT (AR); (SEQ ID NO:2)

GUGAAGUUGGGCAUGACUAdTdT, (SEQ ID NO:3)

UACAAGGACUUCUGCAUCCdTdT (HB-EGF); (SEQ ID NO:4)

AACACUGUGAGUGGUGCCGdTdT, (SEQ ID NO:5)

GAAGCAGGCCAUCACCGCCdTdT (TGFa); (SEQ ID NO:6)

AAAGUUUGCUUGGCACACCUUdTdT, (SEQ ID NO:7)

AAAGUAAGGCCCAGGAGUGUUdTdT, (SEQ ID NO:8)

AACAUAGAGCCACUUUGGAGAdTdT (TACE); (SEQ ID NO:9)

CCUCGCUGCAAAGAAUGUGdTdT (ADAM12), (SEQ ID NO:10)

GACCUUGAUACGACUGCUGdTdT (ADAM12); (SEQ ID NO:11)

CGUACGCGGAAUACUUCGAdTdT (control, GL2). (SEQ ID NO:12)

Specific silencing of targeted genes was confirmed by Western blot (TACE) and RT-PCR analysis. RNA isolated using RNeasy Mini Kit (Qiagen, Hilden, Germany) was reverse transcribed using AMV Reverse Transcriptase (Roche, Mannheim, Germany). PuReTaq Ready-To-Go PCR Beads (Amersham Biosciences, Piscataway, N.J.) were used for PCR amplification. Custom primers (Sigma Ark, Steinheim, Germany) were proAR, 5'-tggtgctgtcgctcttgata-3' and (SEQ ID NO:13)

5'-GCCAGGTATTTGTGGTTCGT-3'; proHB-EGF, (SEQ ID NO:14)

5'-TTATCCTCCAAGCCACAAGC-3' and (SEQ ID NO:15)

5'-TGACCAGCAGACAGACAGATG-3'; proTGFa, (SEQ ID NO:16)

5'-TGTTCGCTCTGGGTATTGTG-3' and (SEQ ID NO:17)

(SEQ ID NO:18)

5'-ACTGTTTCTGAGTGGCAGCA-3'; TACE, (SEQ ID NO:19)

5'-CGCATTCTCAAGTCTCCACA-3' and (SEQ ID NO:20)

5'-TATTTCCCTCCCTGGTCCTC-3'; ADAM12, (SEQ ID NO:21)

5'-CAGTTT CAC GGA AAC CCA CT-3' and (SEQ ID NO:22)

5'-GAC CAG AAC ACG TGC TGA GA-3'.

PCR products were subjected to electrophoresis on a 2.5% agarose gel and DNA was visualized by ethidium bromide staining. Location of the products and their sizes were determined by using a 100-bp ladder (GIBCO, Gaithersburg, Md.) under ultraviolet illumination.

1.5 Proliferation and Migration Assays

For the $^3$H-thymidine incorporation assay (5), SCC-15 cells were seeded into 12-well plates at $3 \times 10^4$ cells/well. Upon serum deprivation for 48 h, cells were subjected to pre-incubation and stimulation as indicated. After 18 h cells were pulse-labelled with $^3$H-thymidine (1 µCi/ml) for 4 h, and thymidine incorporation was measured by trichloroacetic acid precipitation and subsequent liquid-scintillation counting.

Analysis of cell motility was performed as described before (13) using a modified Boyden chamber. 24 h after transfection with siRNAs SCC-9 cells were seeded into polycarbonate membrane inserts (6.5 mm diameter and 8 µm pore size) In 24-transwell dishes at $1 \times 10^5$ cells/well in the presence or absence of agonist. The lower chamber was filled with standard medium without FCS containing 10 µg/ml fibronectin as chemoattractant. Cells were permitted to migrate for 36 h. Following incubation, nonmigrated cells were removed from the upper surface of the membranes. The cells that had migrated to the lower surface were fixed and stained with crystal violet. The stained cells were solubilized in 10% acetic acid, absorbance at 570 nm was measured in a micro-plate reader.

2. Results

The GPCR-induced transactivation signal in HNSCC cells is sensitive to broad-spectrum metalloprotease inhibitors such as batimastat (BB94) (13) and marimastat (BB2516; FIG. 1A). Consistent with a ligand-dependent mechanism of EGFR signal transactivation we found that the monoclonal anti-EGFR antibody ICR-3R which prevents binding of EGF-like growth factors to the extracellular domain of the receptor (14) abrogated GPCR- and EGF-induced EGFR tyrosine phosphorylation in SCC-9 cells (FIG. 1A). In contrast, ICR-3R did not interfere with responses triggered by pervanadate, a potent tyrosine phosphatase inhibitor (15) which increases the tyrosine phosphorylation content of many intracellular proteins. Previous reports demonstrating that GPCR-induced EGFR tyrosine phosphorylation requires proteolytic cleavage of HB-EGF (1-3) prompted us to ask whether HB-EGF or other EGF-like growth factors are involved in the EGFR transactivation pathway in head and neck cancer cells. By cDNA microarray analysis we found the expression of HB-EGF, TGFα and AR mRNAs in SCC-4, SCC-9, SCC-15 and SCC-25 cells (data not shown). Moreover, expression and cell surface localization of these ligands were confirmed by flow cytometry using ectodomain specific antibodies (FIG. 1B, representative data shown for SCC-9). Surprisingly, treatment of head and neck cancer cells with LPA (10 μM) or the phorbol ester TPA (1 mM), which acts as a general inductor of shedding events, reduced the cell surface content of endogenous proAR (FIG. 1C). However, in this cellular context, LPA was not able to induce the proteolytic cleavage of proTGFα or proHB-EGF, while stimulation with TPA resulted in ectodomain cleavage of both EGF-like growth factor precursors (data not shown). These findings suggested that LPA stimulation selectively induces shedding of proAR in HNSCC. In addition, batimastat (10 μM) completely abolished LPA-induced ectodomain cleavage of proAR (FIG. 1C) confirming the requirement of metalloprotease activity for proAR shedding. In agreement with the observation that predominantly pertussis toxin (PTX)-sensitive G proteins of the Gi/o family are mediators of LPA-induced EGFR tyrosine phosphorylation (FIG. 1A), PTX (100 ng/mL) partially inhibited proAR shedding at the cell surface of SCC-9 cells (FIG. 1C).

In addition to the decrease of cell-surface proAR, GPCR stimulation resulted in the accumulation of mature AR in cell culture medium as determined by sandwich-ELISA (FIG. 1D). The finding that AR release in response to carbachol was substantially lower compared to LPA stimulation suggested a direct correlation between the amount of released AR and EGFR tyrosine phosphorylation content in response to GPCR ligands (FIG. 1A). Moreover, pre-incubation with batimastat completely prevented GPCR- and TPA-induced accumulation of AR in cell culture medium (FIG. 1D), confirming metalloprotease-dependency of AR release.

We used three approaches to determine if AR function is required for GPCR-induced EGFR tyrosine phosphorylation and downstream cellular responses. First, we used small interfering RNA (siRNA) to silence the endogenous expression of proAR, proHB-EGF and proTGFα in SCC-9 cells. Effcient and specific knockdown of target gene expression was monitored by RT-PCR (FIG. 2A) confirming that gene silencing occurred by mRNA degradation. Concomitantly, the effect of siRNAs on the EGFR transactivation signal was examined. As shown in FIG. 2B, siRNA to proAR completely blocked GPCR-induced EGFR tyrosine phosphorylation. SiRNAs to proHB-EGF and proTGFα, however, did not significantly alter the transactivation signal demonstrating specific requirement for proAR. In addition, we examined whether proAR knockdown affects the GPCR-induced motility of head and neck cancer cells. In fact, proAR siRNA significantly suppressed LPA-induced chemotactic migration in vitro (FIG. 2C).

Second, we examined the effect of AR neutralizing antibodies on EGFR tyrosine phosphorylation by LPA in the squamous cell carcinoma cell lines SCC-4, SCC-9, SCC-15 and SCC-25. The results show that pre-treatment with either a polyclonal goat or a monoclonal mouse antibody raised against the ectodomain of human AR inhibited the EGFR transactivation signal (FIG. 2D, representative data shown for the polyclonal anti-AR antibody in SCC-9 cells). Similar results were obtained upon stimulation of head and neck cancer cells with carbachol (data not shown). In contrast, specific inhibition of HB-EGF by using the diphtheria toxin mutant CRM197 or anti-HB-EGF neutralizing antibodies showed no effect on LPA- or carbachol-induced EGFR transactivation (data not shown).

Third, since AR contains a heparin-binding domain and the glycosaminoglycan heparin prevents AR-triggered mitogenic responses in keratinocytes (16) and MCF-10A cells (17) we evaluated the effect of heparin on the EGFR transactivation signal. As expected, heparin (100 ng/mL) completely blocked EGFR tyrosine phosphorylation caused by LPA (FIG. 2D). Based on these findings we next examined whether AR function is required for SHC activation downstream of the trans-activated EGFR, since tyrosine phosphorylation of the adaptor protein SHC and formation of a SHC-Grb2-Sos complex is known to be a critical step in linking the activated EGFR to the Ras/MAPK cascade (18). In fact, AR blockade completely prevented LPA-induced SHC tyrosine phosphorylation (FIG. 2D) and association with a glutathione-S-transferase (GST) Grb2 fusion protein (FIG. 2E).

Several studies have previously demonstrated that EGFR transactivation is one important mechanism whereby GPCR agonists activate the ERK/MAPK pathway (4,12,19,20). To determine whether AR was required for LPA stimulated ERK/MAPK activation in HNSCC cells, the effect of AR inhibition on ERK1/2 activation was studied. As shown on FIG. 2F, AR neutralizing antibodies, heparin and batimastat prevented LPA-induced ERK activation in SCC-9 and SCC-15 cells. In addition to its mitogenic effect, LPA can act as a survival factor by activating both the ERK/MAPK pathway and the phosphoinositide 3-kinase (PI3K)-dependent phosphorylation of Akt/PKB (21,22). We therefore raised the question whether LPA stimulation induces phosphorylation of Akt/PKB in head and neck cancer cells. The results indicate that LPA markedly increased phosphorylation of Akt/PKB at Ser-473 (FIG. 2F). Moreover, Akt/PKB phosphorylation by LPA was sensitive to PI3K inhibition by wortmannin or LY294002 (data not shown) and was also abrogated by AR blockade or batimastat treatment (FIG. 2F).

To further extend our studies on AR function for growth-promoting GPCR signalling we assessed the effect of AR inhibition on LPA-induced DNA synthesis. As shown in FIG. 2G, HNSCC cells displayed a significant reduction in the rate of DNA synthesis triggered by LPA upon AR inhibition suggesting that a full proliferative response by LPA requires AR. Moreover, batimastat and the EGFR-specific inhibitor tyrphostin AG1478 decreased DNA synthesis by LPA to below basal level. Collectively, these data substantiate the requirement of AR for the generation of an EGFR-characteristic, mitogenic and motility-promoting transactivation signal in HNSCC.

Recent observations have suggested a role of the metalloprotease-disintegrin TACE/ADAM17 in constitutive shedding of proAR and other EGF-like growth factor precursors in mouse fibroblasts (23,24): Moreover, the proteolytic activity of TACE has been shown to be inhibited by the tissue inhibitor of metalloprotease-3 (Timp-3) but not Timp-1 in vitro (25). As TACE is widely expressed in HNSCC cell lines (FIG. 3A) we investigated the effect of Timp-1 and Timp-3 on the EGFR transactivation signal. Indeed, ectopic expression of Timp-3 but not Timp-1 by retroviral transduction inhibited GPCR-induced EGFR tyrosine phosphorylation in SCC-9 cells (FIG. 3B). Furthermore, ectopic expression of dominant negative TACE which lacks the pro- and metalloprotease domain (26) (FIG. 3C) suppressed GPCR-induced proAR cleavage, release of mature AR (FIG. 3D) and EGFR signal transactivation in SCC-9 cells (FIG. 3E). In contrast, neither dominant negative mutants of ADAM10 (3) and ADAM12 (2) which have been shown to be involved in GPCR-triggered proHB-EGF processing nor an analogous ADAM15 mutant affected the GPCR-induced responses (FIG. 3E, representative data shown for ADAM12).

To independently verify the requirement of TACE for the EGFR transactivation pathway in HNSCC we blocked endogenous expression of TACE by RNA interference. Suppression of TACE expression was monitored by RT-PCR and Western blot analysis (FIG. 4A). Interestingly, siRNA-directed inhibition of TACE resulted in the accumulation of proAR at the cell surface of SCC-9 cells (FIG. 4B) supporting the view that TACE is involved in basal proAR ectodomain processing. In addition, TACE siRNA specifically suppressed GPCR-induced EGFR, SHC, ERK/MAPK and Akt/PKB activation (FIG. 4C). Finally, TACE siRNA also prevented migration of SCC-9 cells in response to LPA (FIG. 4D).

3. Discussion

An increasing amount of experimental evidence supports the concept that the EGFR functions as a central integrator of diverse GPCR signals which are thereby funnelled to downstream pathways (4,6,12). The data presented here support an unexpected mechanism of EGFR transactivation in human cancer cells and identify a novel biological function for TACE in GPCR signalling. Our results demonstrate that GPCR-induced activation of TACE has biological consequences that can be attributed to an increase in the amount of free AR. Other mechanisms, in which HB-EGF-dependent transactivation of the EGFR is mediated by ADAM10 in lung epithelial cells (3) and COS-7 cells (27) or by ADAM12 in cardiomyocytes (2) have been described. This is the first demonstration, however, that transmembrane proAR is cleaved in response to GPCR stimulation and also that AR is functionally relevant for mediating hallmark cancer cell characteristics by GPCR agonists. We demonstrate that TACE-dependent AR release is a prerequisite to GPCR-induced EGFR stimulation, activation of the ERK/MAPK pathway, phosphorylation of Akt/PKB, induction of cell proliferation and migration.

How TACE is activated by heterotrimeric G proteins is not known. Although ERK has been shown to bind to and phosphorylate the cytoplasmic domain of TACE at threonine 735 in response to TPA stimulation (28), GPCR-induced AR release and EGFR tyrosine phosphorylation is insensitive to MEK inhibitors in HNSCC cells (unpublished observation) suggesting ERK not to be involved upstream of the EGFR. An important issue of future studies will be to determine how GPCR signal transmission is defined to be mediated by either ADAM10/HB-EGF, ADAM12/HB-EGF or TACE/AR modules in a cell-type or physiology-dependent manner. Thus, our experimental results represent compelling evidence for the relevance of physiologically important GPCR ligands, TACE and AR in the mediation of critical cancer cell characteristics.

EXAMPLE 2

Production and Characterization of Monoclonal Antibodies Against Tace 2.1 Generation of Monoclonal Antibodies Monoclonal antibodies (Mabs) were raised against the metalloprotease-domain of human TACE (ADAM17). Recombinant protein was used for immunization of BALB/c mice (J. H. Peters, H. Baumgarten and M. Schulze, Monoclonale Antikörper-Herstellung und Charakterisierung, Springer-Veriag, 1985, Berlin Heidelberg New York Tokio), Purification of monoclonal antibodies took place with T-Gel™ Adsorbent from Pierce, Rockford, Ill., USA).

2.2 Functional Analysis 8 monoclonal antibodies recognizing the metalloprotease-domain of TACE were identified by ELISA. These antibodies were used for immunoprecipitation of lysates of HEK-293 cells transiently transfected with an eukaryotic expression plasmid encoding TACE tagged with the hemagglutinin epitope (TACE-HA) (31). The monoclonal antibodies 432-2, 400-1, 343-3 and 432-7 specifically immunoprecipitate the mature form of TACE, whereas the α-HA antibody immunoprecipitates predominantly the pro-form of TACE (FIG. 5).

Furthermore, the ability of the monoclonal antibodies to immunoprecipitate endogenous TACE protein from lysates of SCC-9 cells was tested. The MAbs 432-2, 400-1, 343-3 and 432-7 raised against the metalloprotease domain of TACE specifically immunoprecipitate the mature form of TACE and not the pro-form (FIG. 6).

Monoclonal antibodies were tested for their ability to detect TACE on the cell surface of living cells. Antibodies 402-6 and 368-3 showed no cell surface staining, whereas 367-3 showed a weak signal. In contrast, antibodies 343-3, 374-5, 400-1, 432-2 and 432-7 showed a strong signal (FIG. 7).

Finally, we examined the effect of monoclonal TACE antibodies on LPA-induced EGFR tyrosine phosphorylation in the squamous cell carcinoma cell line SCC-9. The results show that pre-treatment with 374-5, 432-2, 400-1 and 367-3 inhibited the EGFR signal transactivation induced by LPA (FIG. 8), whereas direct stimulation of the EGFR with EGF was not affected by pretreatment with monoclonal TACE antibodies (FIG. 9).

REFERENCES

1. Amour, A. et al. TNF-alpha converting enzyme (TACE) is inhibited by TIMP-3. FEBS Lett 435, 39-44. (1998).
2. Asakura, M. et al. Cardiac hypertrophy is inhibited by antagonism of ADAM12 processing of HB-EGF: metalloproteinase inhibitors as a new therapy. Nat Med 8, 35-40. (2002).
3. Bar-Sagi, D. & Hall, A. Ras and Rho GTPases: a family reunion. Cell 103, 227-38. (2000).
4. Carpenter, G. Employment of the epidermal growth factor receptor in growth factor-independent signaling pathways. J Cell Biol 146, 697-702. (1999).
5. Cook, P. W. et al. A heparin sulfate-regulated human keratinocyte autocrine factor is similar or identical to amphiregulin. Mol Cell Biol 11, 2547-57. (1991).
6. Daub, H., Weiss, F. U., Wallasch, C. & Ullrich, A. Role of transactivation of the EGF receptor in signalling by G-protein-coupled receptors. Nature 379, 557-60. (1996).
7. Diaz-Rodriguez, E., Montero, J. C., Esparis-Ogando, A., Yuste, L. & Pandiella, A. Extracellular Signal-regulated Kinase Phosphorylates Tumor Necrosis Factor alpha-converting Enzyme at Threonine 735: A Potential Role in Regulated Shedding. Mol Biol Cell 13, 2031-44. (2002).
8. Eguchi, S., Dempsey, P. J., Frank, G. D., Motley, E. D. & Inagami, T. Activation of MAPKs by angiotensin II in vascular smooth muscle cells. Metalloprotease-dependent EGF receptor activation is required for activation of ERK and p38 MAPK but not for JNK. J Biol Chem 276, 7957-62. (2001).
9. Elbashir, S. M. et al. Duplexes of 21-nucleotide RNAs mediate RNA interference in cultured mammalian cells. Nature 411, 494-8. (2001).
10. Faure, M., Voyno-Yasenetskaya, T. A. & Bourne, H. R. cAMP and beta gamma subunits of heterotrimeric G proteins stimulate the mitogen-activated protein kinase pathway in COS-7 cells. J Biol Chem 269, 7851-4. (1994).
11. Fujiyama, S. et al. Angiotensin AT(1) and AT(2) receptors differentially regulate angiopoietin-2 and vascular endothelial growth factor expression and angiogenesis by modulating heparin binding-epidermal growth factor (EGF)-mediated EGF receptor transactivation. Circ Res 88, 22-9. (2001).
12. Gschwind, A., Prenzel, N. & Ullrich, A. Lysophosphatidic Acid-induced Squamous Cell Carcinoma Cell Proliferation and Motility Involves Epidermal Growth Factor Receptor Signal Transactivation. Cancer Res 62, 6329-6336. (2002).
13. Gschwind, A., Zwick, E., Prenzel, N., Leserer, M. & Ullrich, A. Cell communication networks: epidermal growth factor receptor transactivation as the paradigm for interreceptor signal transmission. Oncogene 20, 1594-600. (2001).
14. Huyer, G. et al. Mechanism of inhibition of protein-tyrosine phosphatases by vanadate and pervanadate. J Biol Chem 272, 843-51, (1997).
15. Johnson, G. R. & Wong, L. Heparan sulfate is essential to amphi-regulin-induced mitogenic signaling by the epidermal growth factor receptor. J Biol Chem 269, 27149-54. (1994).
16. Keates, S. et al. cag+*Helicobacter pylori* induce transactivation of the epidermal growth factor receptor in AGS gastric epithelial cells. J Biol Chem 276, 48127-34. (2001).
17. Kinsella, T. M. & Nolan, G. P. Episomal vectors rapidly and stably produce high-titer recombinant retrovirus. Hum Gene Ther 7, 1405-13. (1996).
18. Kodama, H. et al. Role of EGF Receptor and Pyk2 in Endothelin-1-induced ERK Activation in Rat Cardiomyocytes. J Mol Cell Cardiol 34, 139-50. (2002).
19. Lemjabbar, H. & Basbaum, C. Platelet-activating factor receptor and ADAM10 mediate responses to *Staphylococcus aureus* in epithelial cells. Nat Med 8, 41-6. (2002).
20. Marinissen, M. J. & Gutkind, J. S. G-protein-coupled receptors and signaling networks: emerging paradigms. Trends Pharmacol Sci 22, 368-76. (2001).
21. Massague, J. & Pandiella, A. Membrane-anchored growth factors. Annu Rev Biochem 62, 515-41. (1993).
22. Mateo, C. et al. Humanization of a mouse monoclonal antibody that blocks the epidermal growth factor receptor: recovery of antagonistic activity. Immunotechnology 3, 71-81. (1997).
23. Peschon, J. J. et al. An essential role for ectodomain shedding in mammalian development. Science 282, 1281-4. (1998).
24. Pierce, K. L. et al. Epidermal growth factor (EGF) receptor-dependent ERK activation by G protein-coupled receptors: a co-culture system for identifying intermediates upstream and downstream of heparin-binding EGF shedding. J Biol Chem 276, 23155-60. (2001).
25. Prenzel, N. et al. EGF receptor transactivation by G-protein-coupled receptors requires metalloproteinase cleavage of proHB-EGF. Nature 402, 884-8. (1999).
26. Sautin, Y. Y., Crawford, J. M. & Svetlov, S. I. Enhancement of survival by LPA via Erk1/Erk2 and PI 3-kinase/Akt pathways in a murine hepatocyte cell line. Am J Physiol Cell Physiol 281, C2010-9. (2001).
27. Solomon, K. A., Pesti, N., Wu, G. & Newton, R. C. Cutting edge: a dominant negative form of TNF-alpha converting enzyme inhibits proTNF and TNFRII secretion. J Immunol 163, 4105-8. (1999).
28. Sunnarborg, S. W. et al. Tumor necrosis factor-alpha converting enzyme (TACE) regulates epidermal growth factor receptor ligand availability. J Biol Chem 31, 31 (2002).
29. Yan, Y., Shirakabe, K. & Werb, Z. The metalloprotease Kuzbanian (ADAM10) mediates the transactivation of EGF receptor by G protein-coupled receptors. J Cell Biol 158, 221-6. (2002).
30. Yart, A et al. A function for phosphoinositide 3-kinase beta lipid products in coupling beta gamma to Ras activation in response to lysophosphatidic acid. J Biol Chem 26, 26 (2002).
31. Pati, U. K. Novel vectors for expression of cDNA encoding epitope-tagged proteins in mammalian cells. Gene 114, 285-288 (1992).

The invention claimed is:

1. A method for modulating transactivation of receptor tyrosine kinases by G-protein or G protein-coupled receptor mediated signal transduction in a cell comprising applying antibodies or antigen-binding antibody fragments or fragments of antibodies which contain at least one antigen-binding site to specifically inhibit the activity of amphiregulin and optionally TACE/ADAM17.

2. The method of claim 1 wherein the cell is a human cell.

3. The method of claim 1 wherein the cell is a carcinoma cell.

4. The method of claim 3 wherein the cell is a squamous carcinoma cell.

5. The method of claim 1 wherein the inhibition comprises application of antibodies or antibody fragments directed against amphiregulin and optionally TAGE/ADAM17.

6. A method for the treatment of a disorder which is caused by or associated with a transactivation of receptor tyrosine kinases by G protein or G protein-coupled receptor mediated signal transduction comprising administering a subject in need thereof an effective amount of antibodies or antiqen-binding antibody fragments or fraqments of antibodies which contain at least one antigen-binding site to specifically inhibit amphiregulin and optionally a specific inhibitor of TACE/ADAM17.

7. The method of claim 1, wherein said fragments are proteolytic antibody fragments selected from the group consisting of Fab, Fab', F(ab')2, or scFv fragments.

* * * * *